US010912883B2

(12) United States Patent
McCawley et al.

(10) Patent No.: US 10,912,883 B2
(45) Date of Patent: Feb. 9, 2021

(54) GAS-POWERED FLUID INJECTION SYSTEM

(71) Applicant: ALTAVIZ, LLC, Irvine, CA (US)

(72) Inventors: Matthew McCawley, San Clemente, CA (US); Andrew Schieber, Laguna Niguel, CA (US); Matthew Flowers, Aliso Viejo, CA (US); Jack R. Auld, Laguna Niguel, CA (US); Marcus Souza, Costa Mesa, CA (US)

(73) Assignee: ALTAVIZ, LLC, Irvine, CA (US)

( * ) Notice: Subject to any disclaimer, the term of this patent is extended or adjusted under 35 U.S.C. 154(b) by 220 days.

(21) Appl. No.: 16/180,001

(22) Filed: Nov. 4, 2018

(65) Prior Publication Data

US 2019/0175825 A1 Jun. 13, 2019

Related U.S. Application Data

(60) Provisional application No. 62/581,696, filed on Nov. 4, 2017.

(51) Int. Cl.
*A61M 37/00* (2006.01)
*A61M 5/155* (2006.01)
(Continued)

(52) U.S. Cl.
CPC .......... *A61M 5/155* (2013.01); *A61M 5/2046* (2013.01); *A61M 5/2053* (2013.01);
(Continued)

(58) Field of Classification Search
CPC .. A61M 2005/1401; A61M 2005/2485; A61M 5/155; A61M 5/2046; A61M 5/2053; A61M 5/3158; A61M 5/482
See application file for complete search history.

(56) References Cited

U.S. PATENT DOCUMENTS

| 2003/0233070 A1* | 12/2003 | De La Serna | .......... | F16K 17/30 604/141 |
| 2005/0000711 A1* | 1/2005 | Hurlstone | ............... | A61M 5/30 173/19 |

(Continued)

OTHER PUBLICATIONS

Acquaviva, Laure, European Patent Office, International Search Report for corresponding International Application No. PCT/US2018/059117, dated Feb. 12, 2019, 8 pages.
(Continued)

*Primary Examiner* — Rebecca E Eisenberg
(74) *Attorney, Agent, or Firm* — William A. English; Vista IP Law Group LLP

(57) ABSTRACT

Gas-powered fluid injection systems and methods are disclosed, e.g., for delivering fluids into a patient's body. An injection device comprises a driver housing which forms and/or encloses a gas pressure source, an actuation piston driven by the gas pressure source and a hydraulic fluid pressurized by movement of the actuation piston. The hydraulic fluid flows through an adjustable valve into a plunger lumen which pushes a plunger of a fluid dispensing device, such as a syringe, to dispense an injection fluid, such as a medicament. The injection device has a movable plunger sleeve which receives the plunger of the fluid dispensing device. The plunger sleeve is moved during the activation and de-activation of the injection device such that it relieves residual pressure in the fluid dispensing device thereby preventing the fluid dispensing device from continuing to dispense injection fluid after the injection device has been de-actuated.

14 Claims, 10 Drawing Sheets

(51) Int. Cl.
*A61M 5/20* (2006.01)
*A61M 5/48* (2006.01)
*A61M 5/315* (2006.01)
*A61M 5/24* (2006.01)
*A61M 5/14* (2006.01)

(52) U.S. Cl.
CPC .......... *A61M 5/3158* (2013.01); *A61M 5/482* (2013.01); *A61M 2005/1401* (2013.01); *A61M 2005/2485* (2013.01)

(56) References Cited

U.S. PATENT DOCUMENTS

| | | | | |
|---|---|---|---|---|
| 2005/0267403 | A1* | 12/2005 | Landau | A61M 5/30 604/70 |
| 2007/0149925 | A1* | 6/2007 | Edwards | G16H 20/17 604/141 |
| 2011/0245866 | A1* | 10/2011 | Cassingham | A61B 17/00491 606/213 |
| 2011/0301538 | A1* | 12/2011 | Stammen | A61M 5/14526 604/121 |
| 2013/0317478 | A1* | 11/2013 | Auld | A61M 5/2046 604/506 |
| 2017/0119522 | A1 | 5/2017 | Auld et al. | |
| 2017/0312422 | A1* | 11/2017 | Auld | A61M 5/2053 |
| 2019/0167906 | A1* | 6/2019 | Auld | A61M 5/2066 |

OTHER PUBLICATIONS

Walther, Manuel, European Patent Office, Written Opinion for corresponding International Application No. PCT/US2018/059117, dated Feb. 12, 2019, 10 pages.

* cited by examiner

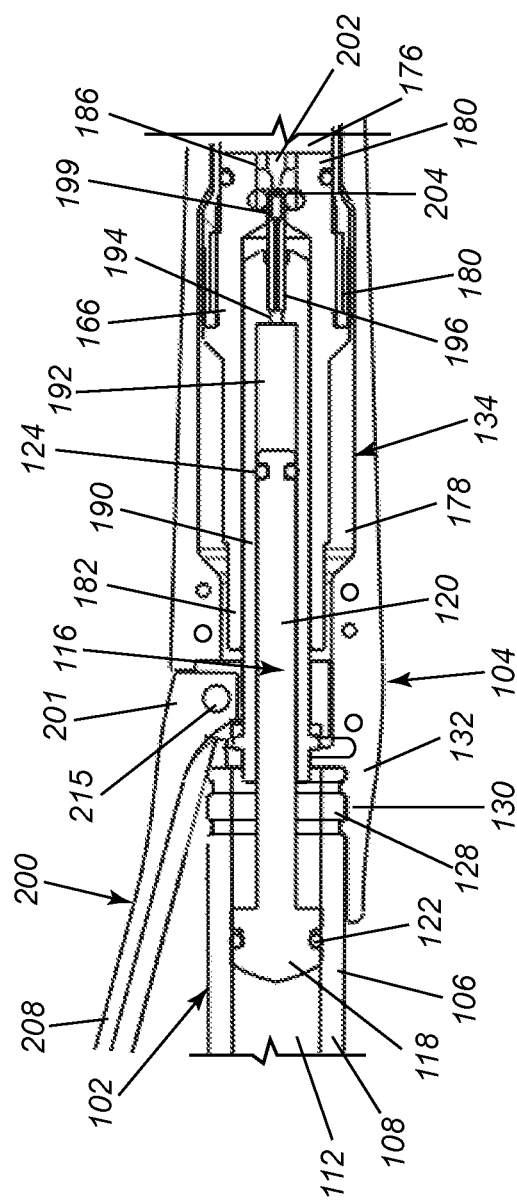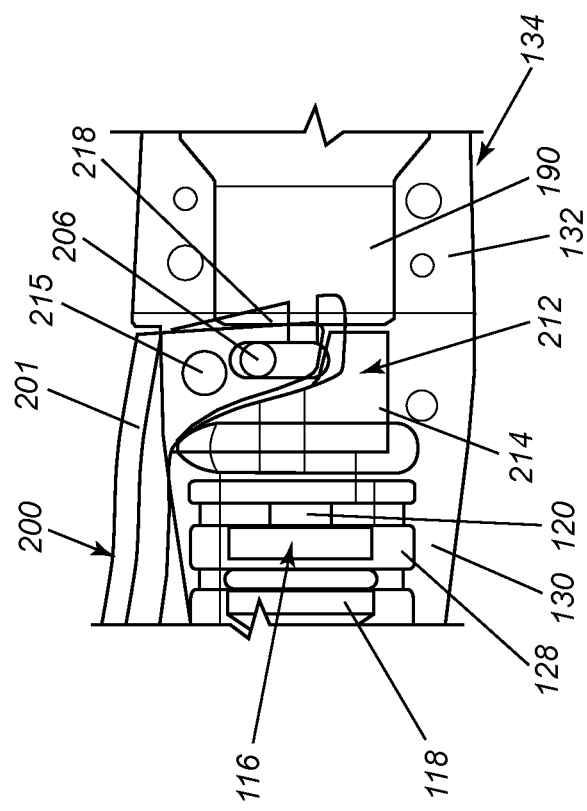

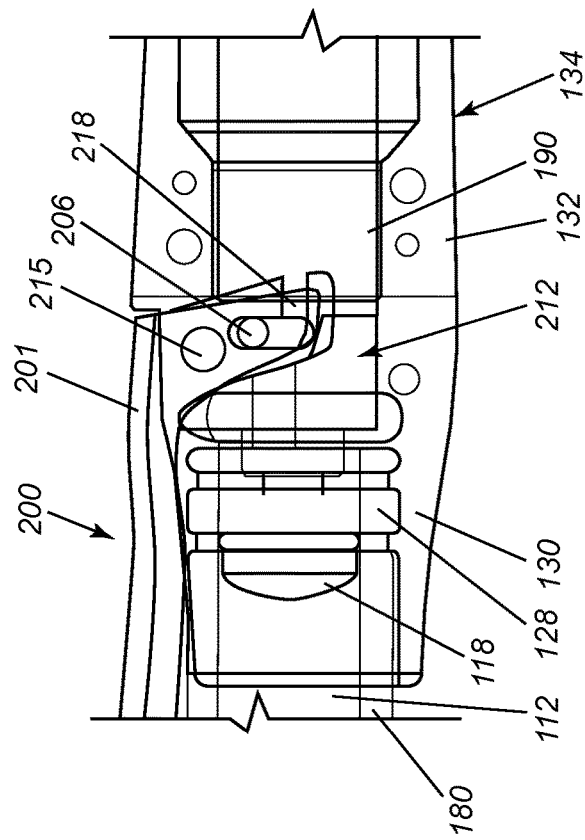
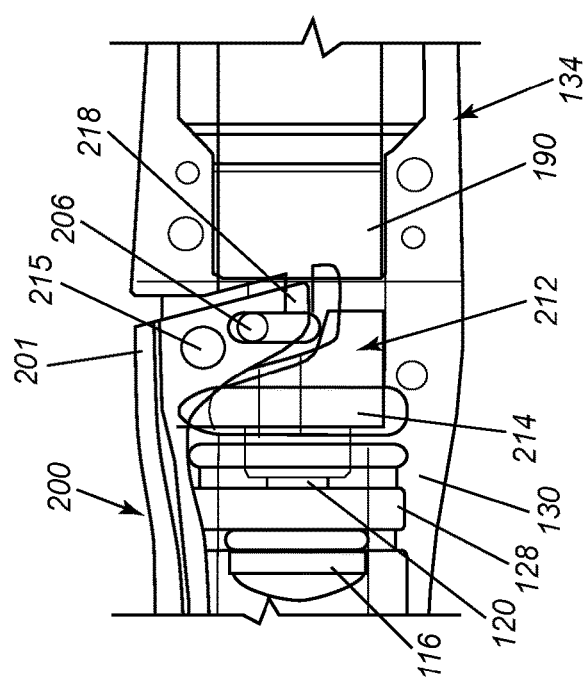

GAS-POWERED FLUID INJECTION SYSTEM

RELATED APPLICATION DATA

The present application claims benefit of U.S. provisional application Ser. No. 62/581,696, filed Nov. 4, 2017, the entire disclosure of which is expressly incorporated by reference herein.

TECHNICAL FIELD

The inventions described herein generally relate to devices and methods for delivering fluids and, more particularly, to gas-powered fluid injections systems, such as a gas-powered syringe device, e.g., for delivering fluids into a patient's body, and to methods for using such systems.

BACKGROUND

There are many applications requiring controlled delivery of a medicament or viscous fluid while maintaining precise position control of the delivery needle to deliver a precise volume of fluid in a precise location. In many of these cases, the desired therapeutic effect is completely dependent on meeting all of these objectives.

In particular, during delivery of various fluids into a patient's body using a syringe and needle, it is generally desirable for a clinician to accurately position the tip of the needle, apply force to the syringe's plunger to develop desired flow of the therapeutic fluid, and control the flow rate of the fluid. For highly viscous fluids, the forces required to develop the fluid flow can be very high requiring significant hand strength on the part of the clinician. In most cases, fine position control is also required. Typical syringes are held and actuated at the end completely opposite to the end that discharges the fluid, which makes it difficult to maintain positional accuracy of the tip. Typically, the clinician uses the same hand to position the syringe that is used to develop and control the flow. Fine motor skills are preferred for controlling the position and flow rate, while gross motor skills are required for developing flow and maintaining flow rate in viscous materials, and, consequently, current syringe and needle systems compromise these skills.

Therefore, devices and methods for delivering fluids into a patient's body with increased precision and/or control would be useful.

SUMMARY

The inventions disclosed herein generally relate to devices and methods for delivering fluids and, more particularly, to gas-powered fluid injection systems, e.g., for delivering fluids into a patient's body, and to methods for using such systems.

In one exemplary embodiment, an injection device for injecting fluid according to the present invention comprises a driver housing containing an innovative, gas powered driver assembly. The driver housing has a proximal end, a distal end, and a receiver on the proximal end of the driver housing configured to attach to a fluid dispensing device, such as a syringe having a syringe housing having a syringe cavity and a plunger slidably received in the syringe cavity.

A gas pressure source is disposed in the driver housing. An actuation piston is slidably disposed in the driving housing such that it is axially movable relative to the driver housing. The piston has a proximal surface exposed to pressure from the gas when delivered from the gas pressure source and a distal surface exposed to a hydraulic fluid in a hydraulic fluid reservoir. The driver housing has a hydraulic fluid reservoir containing hydraulic fluid disposed within the driver housing.

A valve body is slidably disposed in the driver housing such that the valve body is axially movable relative to the driver housing. The valve body has a proximal end and a distal end. The valve body has a sleeve cavity for slidably receiving a plunger sleeve. The sleeve cavity has a distal end having an opening for receiving the plunger sleeve, and a proximal end having a fluid passage connecting to a valve.

A plunger sleeve is slidably disposed in the sleeve cavity such that the plunger sleeve is movable axially relative to the valve body. The plunger sleeve has a plunger lumen for slidably receiving a plunger of a fluid dispensing device, such as a syringe. The plunger lumen is in fluid communication with the fluid passage such that the valve is in a flow path between the plunger lumen and the fluid passage.

The valve is disposed in the driver housing. The valve is configured such that, when the valve is open, the valve allows the hydraulic fluid to flow between the hydraulic fluid reservoir and the plunger lumen via the fluid passage; and when the valve is closed, the valve prevents hydraulic fluid from flowing between the hydraulic fluid reservoir and the plunger lumen via the fluid passage. The valve is coupled to the valve body such that axial movement of the valve body opens and closes the valve.

The injection device has a lever or other actuator pivotally coupled to the driver housing. The lever is also coupled to the valve body and the plunger sleeve such that pivotable movement of the lever moves the valve body to open and close the valve and pivotable movement of the lever also moves the plunger sleeve axially relative to the driver housing.

The injection device operates to drive a fluid dispensing device to dispense an injection fluid out of the fluid dispensing device. The injection device is actuated by allowing pressurized gas from the gas pressure source to flow to the actuation piston thereby pressurizing the proximal surface of the piston. For example, the gas pressure source may be opened to allow gas to flow out of the gas pressure source by puncturing a seal in a gas canister containing the pressurized gas, or opening a gas valve on the gas pressure source. In another aspect, the lever may be coupled to an actuator which opens the gas pressure source. For instance, in still another aspect, the injection device may have a puncture pin coupled to the valve body such that axial movement of the valve body in response to pivotable movement of the lever causes the puncture pin to rupture a seal on the gas pressure source. Thus, the injection device is actuated by pivoting the lever from a pre-activation position to an actuation position which moves the valve body axially causing the puncture pin to puncture the gas seal. The axial movement of the valve body also opens the valve. The pivoting of the lever also moves the plunger sleeve axially in the proximal direction.

The gas pressure exerts pressure on the proximal surface of the piston causing the piston to move distally such that the distal surface of the piston pressurizes the hydraulic fluid. This causes the hydraulic fluid to flow through the now open valve, through the fluid passage into the plunger lumen. The pressurized hydraulic fluid in the plunger lumen pushes a plunger of a fluid dispensing device received in the plunger lumen which causes the fluid dispensing device to dispense an injection fluid, such as a drug or medicament.

In another aspect, the lever may be adjusted to adjust the flow rate of injection fluid being dispensed by the fluid dispensing device. The lever may be adjusted by pivoting the lever to move the valve body, thereby adjusting the opening of the valve to adjust the flow rate of hydraulic fluid flowing through the valve. In turn, adjusting the flow rate of hydraulic fluid flowing through the valve adjusts the speed at which the plunger is pushed distally by the hydraulic fluid, thereby adjusting the flow rate of injection fluid being dispensed by the fluid dispensing device.

In another aspect, when the lever is returned to the pre-actuation position, the valve body returns to the pre-actuation position. The valve body may be forced back to the pre-actuation position by a valve body biasing spring, and/or by the lever exerting a force directly on the valve body. This movement of the valve body closes the valve, which stops the flow of hydraulic fluid through the fluid passage into the plunger lumen which, in turn, stops the movement of the plunger in the plunger lumen. The movement of the lever back to the pre-activation position also moves the plunger sleeve proximally (i.e., away from the plunger).

The movement of the plunger sleeve proximally creates space behind the plunger which relieves the pressure of the hydraulic fluid in the plunger lumen. This allows the plunger to move proximally due to residual pressure of the injection fluid in the fluid dispensing device. This innovative pressure relief feature prevents the residual pressure from continuing to dispense injection fluid out of the fluid dispensing device. In the absence of this pressure relief function, the residual pressure of the injection fluid would otherwise cause injection fluid to slowly flow out of the fluid dispensing device after the lever has been moved back to the pre-activation position (the post-actuation, stop dispensing position).

In another aspect of the present invention, the injection device may further comprise a syringe or other injector device coupled to the driver housing. The syringe has a syringe housing and a plunger slidably disposed in the syringe housing. The syringe housing has a proximal end, a distal end, and a syringe cavity extending from the proximal end to an outlet port on the distal end of the syringe housing. The plunger is slidably disposed in the syringe cavity. The plunger includes a plunger rod and a plunger piston on a distal end of the plunger rod. The proximal end of the syringe housing is attached to the receiver of the driver housing and a proximal portion of the plunger rod extends proximally out of the syringe cavity and into the plunger lumen of the plunger sleeve.

In another exemplary embodiment, another injection device comprises a driver housing containing a gas powered driver assembly. The driver housing has a proximal end, a distal end, and a gas chamber proximate the proximal end configured to contain a pressurized gas, and a gas seal which seals a gas outlet of the gas chamber. The driver housing has a piston chamber adjacent and distal of the gas chamber and a fluid flow path connecting to the gas outlet. The driver housing has a valve body chamber adjacent and distal of the piston chamber and a hydraulic fluid reservoir adjacent and distal of the piston chamber containing a hydraulic fluid. The driver housing also has a receiver on the distal end of the driver housing configured to attach to a fluid dispensing device.

A piston is slidably disposed in the piston chamber. The piston has a proximal surface exposed to pressure from the pressurized gas when delivered from the gas chamber through the gas outlet, and a distal surface exposed to the hydraulic fluid in the hydraulic fluid reservoir. A valve body is slidably disposed in the valve body chamber. The valve body has a proximal end and a distal end. The valve body has a sleeve cavity extending proximally from the distal end of the valve body to a fluid passage at a proximal end of the sleeve cavity. The fluid passage is connected to a flow control valve.

A plunger sleeve is slidably disposed in the sleeve cavity of the valve body such that the sleeve is movable axially relative to the valve body. The plunger sleeve has a plunger lumen for receiving a plunger of a fluid dispensing device. The plunger lumen is in fluid communication with the fluid passage such that the valve is in a flow path between the plunger lumen and the fluid passage.

The valve is coupled to the valve body such that axial movement of the valve body opens and closes the valve. The valve is configured such that, when the valve is open, the valve allows the hydraulic fluid to flow between the hydraulic fluid reservoir and the plunger lumen via the fluid passage, and, when the valve is closed, the valve prevents hydraulic fluid from flowing between the hydraulic fluid reservoir and the plunger lumen via the fluid passage.

A lever or other actuator is pivotally coupled to the driver housing. The lever is also coupled to the plunger sleeve and the valve body such that pivotable movement of the lever moves the valve body axially to open and close the valve and movement of the lever also moves the plunger sleeve axially relative to the driver housing.

In another aspect, the lever is configured such that, movement of the lever from a pre-activation position, in which the valve body closes the valve and the plunger sleeve is in a pre-activation proximal position, to an activation position, opens the gas seal, opens the valve and moves the plunger sleeve distally such that the plunger sleeve moves distally away from the valve. Movement of the lever back towards the pre-activation position from the activation position moves the valve body such that it closes the valve, and also moves the plunger sleeve proximally thereby relieving residual pressure within the sleeve cavity.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures, wherein like reference numerals refer to like elements and the description for like elements shall be applicable for all described embodiments wherever relevant.

FIG. 8 is an enlarged side, cross-sectional view of a portion of the injection device of FIG. 1 in a post-actuation position after having been activated, according to one exemplary embodiment;

FIG. 9 is an enlarged, side, transparent view of a portion of the injection device of FIG. 1 in a pre-actuation position, according to one exemplary embodiment;

FIG. 10 is an enlarged, side, transparent view of a portion of the injection device of FIG. 1 as it is being actuated from a pre-activation position to an activation position, according to one exemplary embodiment;

FIG. 11 is an enlarged, side, transparent view of a portion of the injection device of FIG. 1 in an activation position, according to one exemplary embodiment;

DETAILED DESCRIPTION OF THE EXEMPLARY EMBODIMENTS

Figure 1:
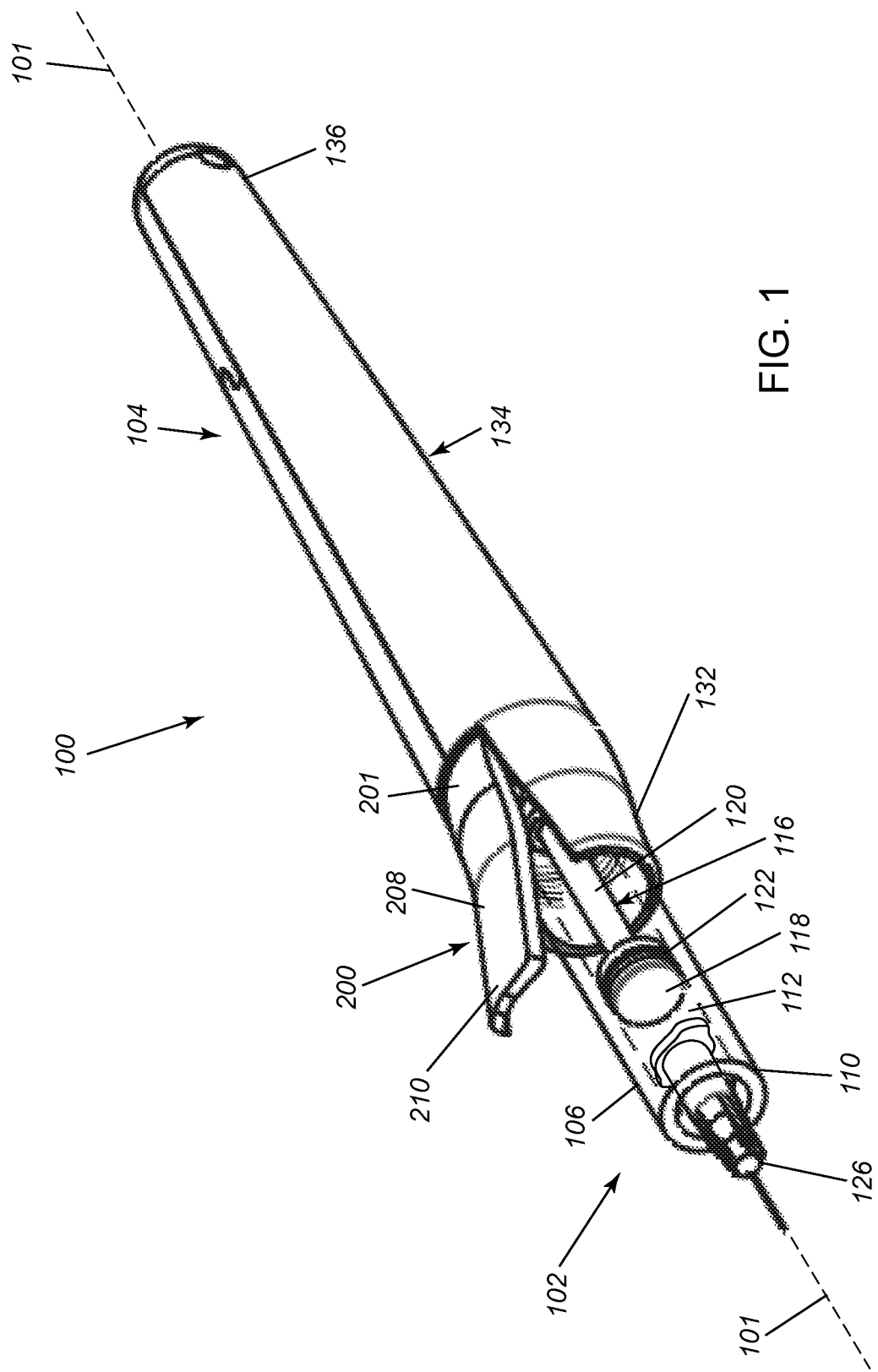
FIG. 1 is a perspective view of an exemplary embodiment of an injection device in a pre-activation position.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary, or the following detailed description.

Certain terminology may be used in the following description for the purpose of reference only, and thus are not intended to be limiting. For example, terms such as "upper," "lower," "above," and "below" refer to directions in the drawings to which reference is made. Terms such as "proximal," "distal," "front," "back," "rear," and "side" describe the orientation and/or location of portions of the component within a consistent but arbitrary frame of reference, which is made clear by reference to the text and the associated drawings describing the component under discussion. Such terminology may include the words specifically mentioned above, derivatives thereof, and words of similar import.

For example, as used herein, the terms "front" and "distal" refer to parts of the subject device that are located further away from the user (e.g., clinician) of the device, e.g., during an injection operation. As used herein, the terms "rear" and "proximal" refer to the parts of the device that are located closer to the user (e.g., clinician) of the device, e.g., during an injection operation.

There are many applications where controlled delivery of a medicament is desired while maintaining precise position control of the delivery needle to deliver a precise volume of fluid in a precise location. The devices and methods described herein may facilitate precise delivery of medicaments into a patient's body, e.g., one or more viscous fluids or other flowable material for various therapeutic and/or diagnostic purposes. As used herein, "medicament" is intended to refer to any such fluids or materials, such as those described in the examples herein. For example, below is a summary of exemplary applications where the devices and methods described herein may be used to deliver fluids into a patient's body.

Ophthalmology: The gas-powered fluid injection system 100 (also referred to as injector device 100, for short) shown in FIG. 1, may be used for sub-retinal injections in the treatment of several disease conditions of an eye. The injector 100 may include a syringe 102 and a syringe driver 104.

Treatment of retinal vein occlusions: Multiple indications may be treated by the administration of therapeutic agents into the sub-retinal space in the eye. In cases of branch retinal vein occlusion (BRVO) and central retinal vein occlusion (CRVO), 50 to 150 µL of tissue plasminogen activator (TPA) may be administered through relatively small hypodermic needles (e.g., not more than 41 gauge) to dissolve blood clots formed by sub-retinal hemorrhages during the course of retinal surgery. In these cases, the ophthalmic surgeon may place the tip under the surface of a patient's retina and slowly inject the TPA to create a bleb of medicament that dissolves the coagulated blood over the course of a few days.

Gene therapy for the treatment of macular degeneration: Age-related macular degeneration (AMD) is a leading cause of vision loss and blindness among the elderly. AMD is a progressive ocular disease of the part of the retina, called the macula, which enables people to read, visualize faces, and drive. The disease initially causes distortion in central vision, and eventually leads to legal blindness. A layer of cells at the back of the eye, called the retinal pigment epithelium (RPE), provides support, protection, and nutrition to the light sensitive cells of the retina, i.e., the photoreceptors consisting of rods and cones. The dysfunction and/or loss of these RPE cells play a critical role in the loss of the photoreceptors and hence blindness in AMD. Recent advances in research show promise in new therapies to treat AMD. Human embryonic stem cells, gene therapies, complement factors, and viral vectors are under development with early stage animal studies and/or clinical trials. Some of these treatments require administration of the cells into targeted areas of the eye including the sub-retinal space or the suprachoroidal space with exquisite control over position, volumetric delivery rate, and/or total volume.

Aesthetic Medicine: The goals in aesthetic medicine are generally to improve external perception of a person's skin and or external features. There are multiple therapies that require controlled injection of therapeutic agents to achieve their targeted effects.

Neurotoxins: For example, botulinum toxin may be used to temporarily deaden nerves to prevent a person from using muscle groups that create facial wrinkles. The two common areas are the frontalis muscles of the forehead and around the mouth. Botulinum toxin is a low viscosity fluid that requires controlled delivery over volume and precise control over the position so that treatment is limited to a target area to prevent unintended consequences to the patient.

These neurotoxins are low viscosity and are injected with small syringes and/or needles, and require fine motor and position control on the part of the clinician to prevent injection of too much fluid volume or injection into the wrong area, both of which may cause damage to a patient. Because the cross-sectional area of the small syringes are relatively small, high injection pressures may be generated with low plunger forces so control over the injection volume and rate is reduced.

Dermal fillers: Highly viscous fluids, such as hyaluronic acid, may be injected into a patient's skin to increase the volume of the skin, to push out wrinkles, fill voids left by acne scarring or surgical removal of tumors, give volume to lips, and/or fill the upper cheeks. These are typically injected using relatively large syringes that require high plunger forces that the surgeon must manually apply. Simultaneously, the clinician must maintain positional accuracy to hit the desired location and control the delivery rate to minimize patient discomfort.

Fat grafting: In some cases, fat is harvested from one portion of a patient's body, purified and concentrated, and then injected as a filler into an area targeted for cosmetic improvement. Grafted fat may be used as a filler material in the same manner as the other dermal fillers. In "micro" fat grafting, small amounts are used for facial improvements, while more general fat grafting may be used to increase the size of breasts or buttocks. The injection of this material has the same challenges as other dermal fillers as it requires relatively high injection pressures with good control over position and delivery rate.

Referring to FIGS. 1-7, an exemplary embodiment of an injector device 100 is shown for delivering one or more agents into a patient's body, e.g., through the patient's skin. As used herein, "agent" may include one or more therapeutic and/or diagnostic compounds or materials, e.g., in liquid or gaseous form, in solution or suspension, and the like, such as viscous fluids.

Generally, the injector device 100 includes a driver 104 and a syringe or other injection device 102 attached to the driver 104. The syringe 102 includes a syringe housing 106 having a proximal end 108 and a distal end 110, defining a central longitudinal axis 101 of the injector device 100. The syringe housing 106 has a syringe cavity 112 which is open at the proximal end 108 of the housing 106 and which extends distally to an outlet port 114 on the distal end 110 of the housing 106. The syringe cavity 112 is cylindrical in the described embodiment, but may be any suitable shape.

The syringe cavity 112 slidably receives a plunger 116 having a piston 118 and a plunger rod 120 extending distally from the piston 118 such that the piston 118 is attached to a distal end of the plunger rod 120. The syringe cavity 112 distal of the piston 118 defines a reservoir for holding an injection fluid 113 (such as a medicament) to be dispensed and/or injected by the injector device 102. The plunger rod 120 extends proximally out of the end of the proximal end of the syringe cavity 112.

The piston 118 is a cylindrical member, or other suitable shape, to match the syringe cavity 112. The piston 118 has one or more piston seals 122 (e.g., an O-ring seal) that slidably engage the interior surface of the syringe housing 106 within the syringe cavity 112 to allow the piston 118 to move axially within the syringe cavity 112 while providing a fluid-tight seal. Alternative to using a seal 122, the piston 118 may be formed of an elastomeric material that slidably engages the interior surface of the syringe housing 106 within the syringe cavity 112 to allow the piston to move axially within the syringe cavity 112 while providing a fluid-tight seal.

Figure 3:
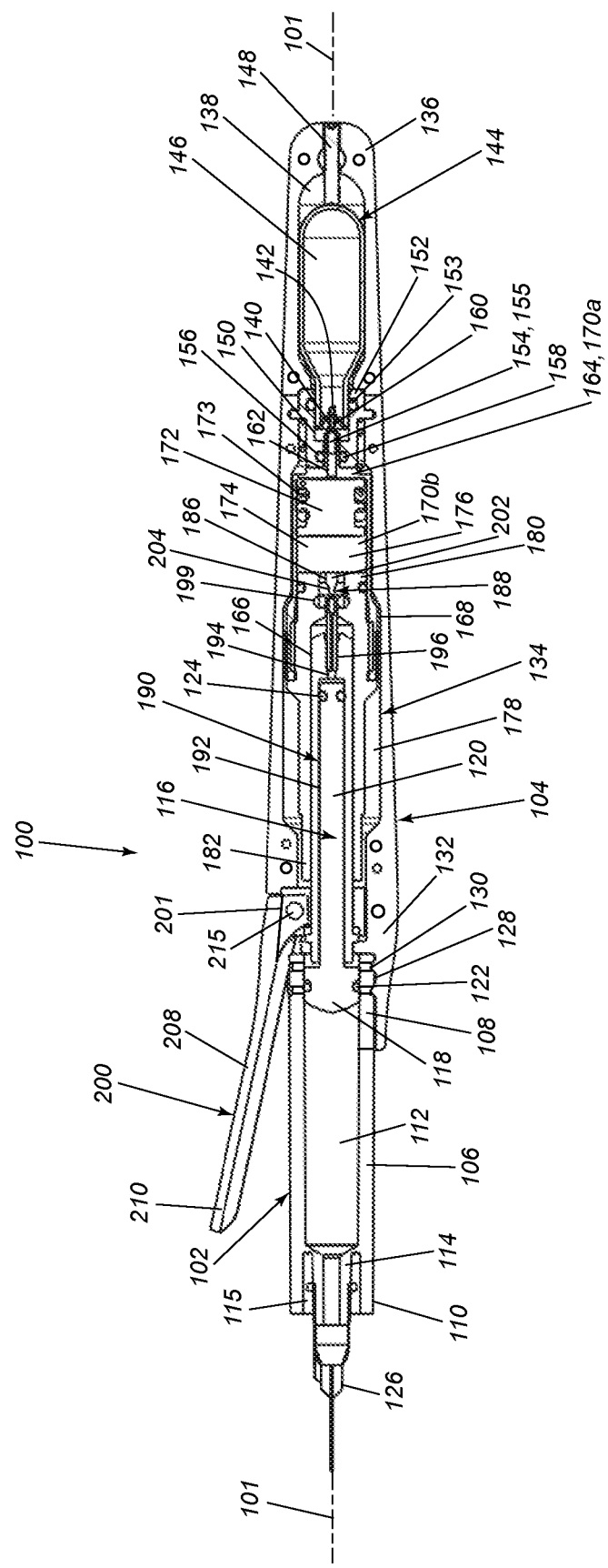
FIG. 3 is a side, cross-sectional view of the injection device of FIG. 1 in a pre-activation position, according to one exemplary embodiment.
Figure 4:
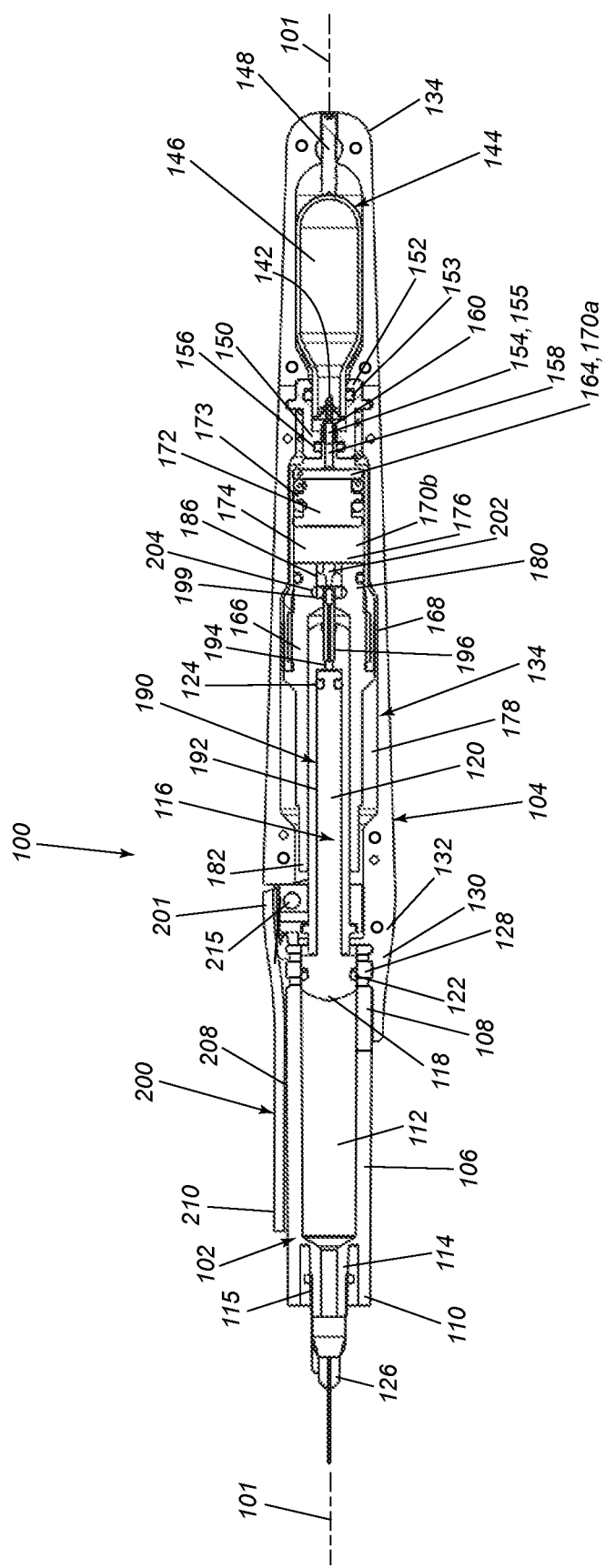
FIG. 4 is a side, cross-sectional view of the injection device of FIG. 1 in an activation position, according to one exemplary embodiment.
Figure 6:
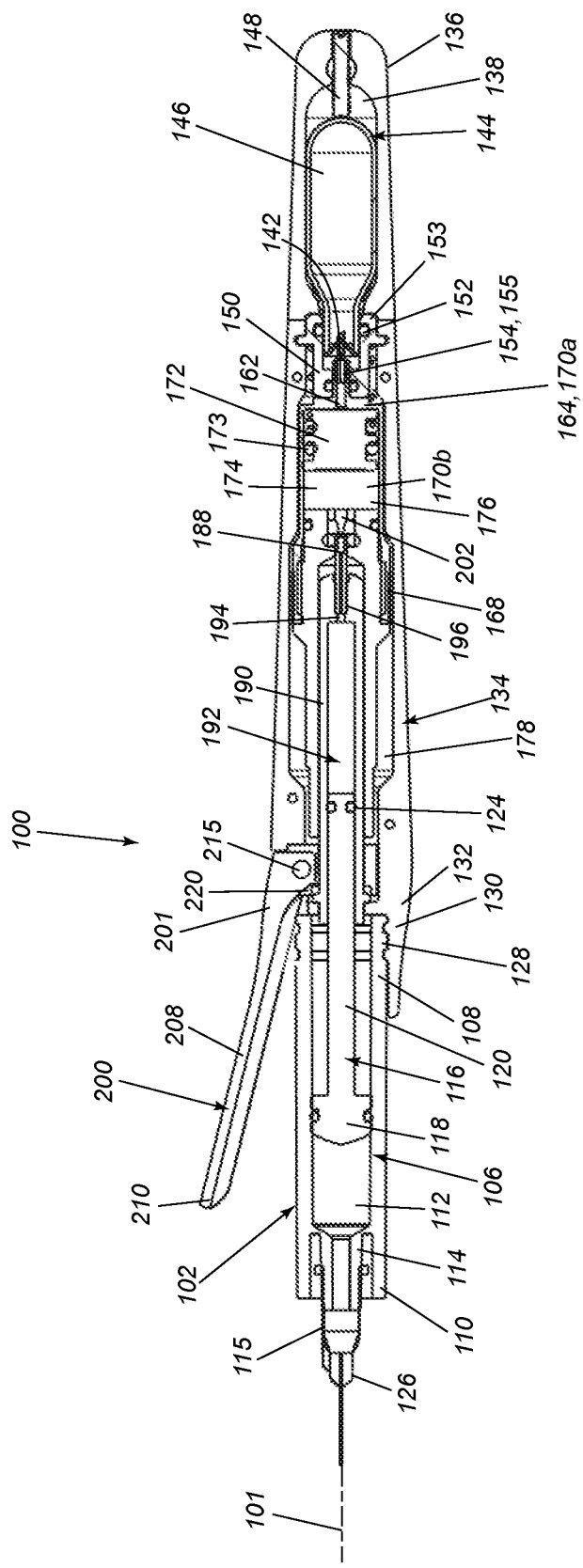
FIG. 6 is a side, cross-sectional view of the injection device of FIG. 1 in a post-actuation position after having been activated, according to one exemplary embodiment.
Figure 7:
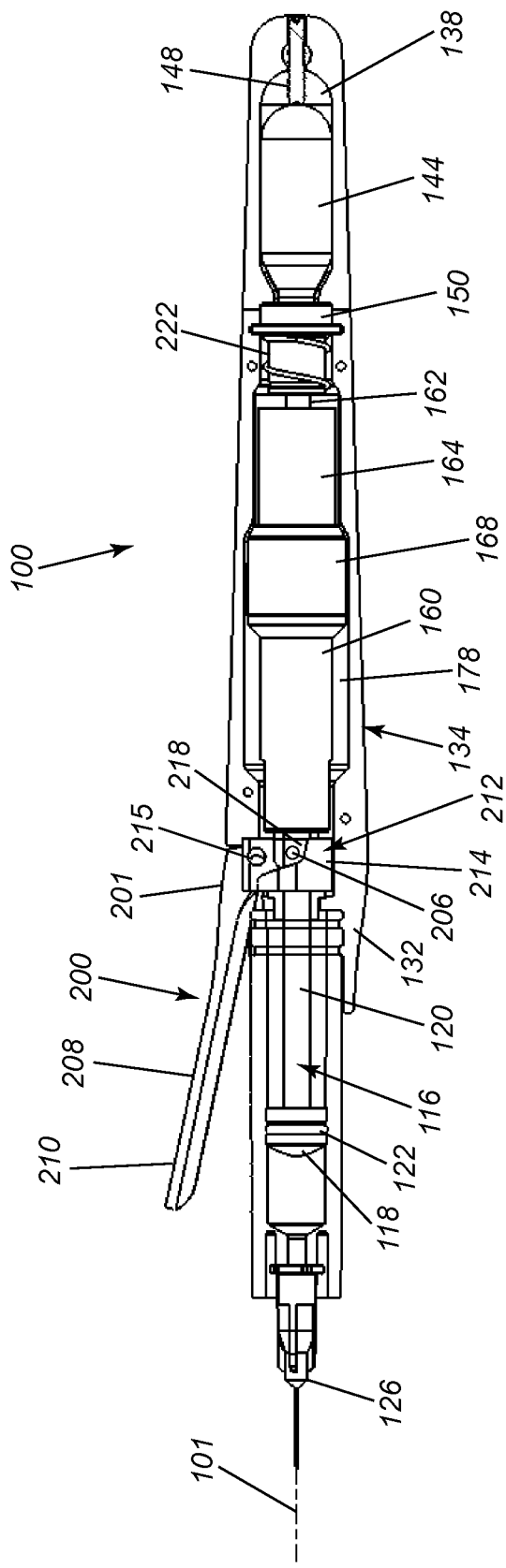
FIG. 7 is a side, partial cross-sectional, partial cut-away view of the injection device of FIG. 1 in a post-actuation position after having been activated, according to one exemplary embodiment.

The plunger 116 is axially movable from a proximal, pre-activation position, as shown in FIG. 3, to a more distal position as shown in FIGS. 6 and 7, to force the fluid in the syringe cavity 112 out through the outlet port 114. The plunger 116, including the piston 118 and seal(s) 122 are compatible and/or inert with respect to the fluid contained within the syringe cavity 112.

The plunger 116 also has a rod seal 124 on the plunger rod 120 at or near a proximal end of the plunger rod 120 that slidably engages a plunger lumen 192 of the syringe driver 104 while providing a fluid tight seal between the plunger rod 120 and the plunger lumen 192.

The outlet port 114 delivers the fluid in the syringe cavity 112 when the plunger 116 is moved axially in the distal direction thereby forcing the fluid in the syringe cavity 112 through the outlet port 114. The outlet port 114 may have a fitting 115 (e.g., a Luer fitting) or other connector for attaching a needle, cannula, or other fluid delivery device to the end of the outlet port 114. In the illustrated embodiment, a needle 126 is attached to the outlet port 114.

The syringe 102 may be attached to the syringe driver 104 by any suitable method. In the illustrated embodiment, the proximal end 108 of the syringe housing 106 has a connector 128 (e.g., grooves, flanges, or threads) which mates to a cooperating connector 130 on a distal end 132 of the driver housing 134. For example, the connectors 128 and 130 may have mating threads or a snap-fit. The mating connectors 128 and 130 may engage such that the syringe 102 is substantially permanently attached to the syringe driver 104, or the connectors 128 and 130 may allow the syringe 102 to be removable coupled to the syringe driver 104. Either way, the syringe 102 and syringe driver 104 may be provided unattached to allow the use of different combinations of syringes and syringe drivers which can then be assembled during manufacturing or immediately before user by a user. Alternatively, the syringe 102 may be integrated together with syringe driver 104 as a unitary assembly (not shown) in which case no connectors 128 and 130 are required. For instance, the syringe housing 106 may be integrated with the driver housing 134 such that the entire injector device 100 is contained in one housing.

Still referring to FIGS. 1-7, the syringe driver 104 includes a driver housing 134 having a proximal end 136 and a distal end 132 which also define the same longitudinal axis 101. The syringe housing 134 has a plurality of chambers within the housing 134, which contain the gas powered driver assembly of the syringe driver 104. More specifically, the driver housing 134 has a gas chamber 138 proximate the proximal end 136 of the syringe housing 134. The gas chamber 138 is configured to contain a pressurized gas 146. The gas chamber 138 has a gas outlet 140 at the distal end of the gas chamber 138. The gas outlet 140 is sealed by a gas seal 142 which can be opened upon activation of the syringe driver 104. In the illustrated embodiment, the gas chamber 138 includes a canister 144 of pressurized gas 146 and the gas seal 142 is a septum 142 which is opened by puncturing the septum 142. A set screw 148 threads through a threaded hole in the proximal end of the syringe housing 134 and bears against a proximal end of the canister 144 in order to secure the gas canister 144 in the gas chamber 138 of the syringe housing 134.

The pressurized gas 146 may be any suitable pressurized fluid, including for example, a two-phase or one-phase gas, such as carbon dioxide, argon, or nitrogen. The pressurized gas 146 from the canister 144 preferably applies a predetermined pressure to the flow path 155 and the actuation piston 172. Additional information regarding canisters that may be included in the syringe drivers herein may be found in U.S. application Ser. No. 15/064,464, filed Mar. 8, 2016, the entire disclosure of which is expressly incorporated by reference herein.

A bulkhead fitting 150 is also contained in the gas chamber 138 distal to the gas outlet 140. The bulkhead fitting 150 has a proximal opening 152 which receives the gas outlet 140. The proximal opening 152 has a seal 153 (e.g., an O-ring seal 154) which provides a fluid-tight seal between the gas outlet 140 and the proximal opening 152. The bulkhead fitting 150 slidably receives a puncture pin assembly 154 which extends axially through the bulkhead fitting 150. The bulkhead fitting 150 has a seal 156 that slidably engages the puncture pin assembly 154 to allow the puncture pin assembly 154 to move axially within the bulkhead fitting 150 while providing a fluid-tight seal between the bulkhead fitting 150 and the puncture pin assembly 154.

The puncture pin assembly 154 includes a gas tube 158, a puncture pin 160 and a junction tube 162. The puncture pin 160 inserts into the lumen of the gas tube 158 and is attached to the gas tube 158. For example, the puncture pin 160 may be attached to the gas tube 158 by press fitting, bonding with adhesive, welding, or other suitable attachment method. The puncture pin 160 is a tube having a lumen and a puncture point on the proximal end of the tube. The puncture pin 160 extends proximally from the gas tube 158 out through the proximal opening 152 of the bulkhead fitting 150 such that the puncture point is proximate the septum 142 of the canister 144. The junction tube 162 inserts into the lumen of the gas tube 158 and is attached to the gas tube, e.g., by press fitting, bonding with adhesive, welding, or other suitable attachment method. The junction tube 162 extends distally from the gas tube 158 into a piston chamber 164.

The distal end of the junction tube 162 is coupled to a valve body 166 such that the puncture pin assembly 154 moves axially with axial movement of the valve body 166. In the illustrated embodiment, the distal end of the junction tube 162 is attached to an actuation housing 168, which is in turn attached to the valve body 166. The puncture pin assembly 154 provides a gas flow path 155 between the gas outlet 140 and a piston chamber 164.

The driver housing 134 has a piston chamber 164 adjacent and distal of the gas chamber 138. The piston chamber 164 includes the actuation housing 168, which forms the wall of the piston chamber 164. The actuation housing 168 has a closed proximal end, except for an opening for the junction tube 162. The junction tube 162 extends through the opening in the closed proximal end and is attached to the closed proximal end, such that the gas flow path 155 extends into the piston chamber 164.

The actuation piston 172 is slidably disposed in the piston chamber 164 such that the actuation piston 172 moves axially within the piston chamber 164, and divides the piston chamber 164 into a proximal region 170a and a distal region 170b. The actuation piston 172 has a proximal surface exposed to the distal region 170b, which is pressurized with the pressurized gas 146 delivered from the canister 144 through the gas flow path 155 when septum 142 is punctured. The actuation piston 172 has a distal surface exposed to a hydraulic fluid 174 in the distal region 170b, which at least partially forms a hydraulic fluid reservoir 176 containing the hydraulic fluid 174. Accordingly, the driver housing 134 includes the hydraulic fluid reservoir 176 which is at least partially formed by the distal region 170b of the piston chamber 164. The actuation piston 172 has one or more seals 173 (e.g., O-ring seals) that slidably engage the interior wall of the piston chamber 164 to allow the actuation piston 172 to move axially within the piston chamber 164 while providing a fluid-tight seal.

The hydraulic fluid 174 may be any suitable fluid that is compatible with materials of the injector device 100, and which is substantially incompressible. In exemplary embodiments, the hydraulic fluid 174 may be an incompressible liquid, such as silicone oil, propylene glycol, glycerin, saline, water, or other substantially incompressible fluids.

The driver housing 134 also has a valve body chamber 178 adjacent and distal of the piston chamber 164. The valve body 166 is slidably disposed in the valve body chamber 178 such that the valve body 166 is axially movable relative to the valve body chamber 178 of the driver housing 134. The valve body 166 has a proximal end 180 and a distal end 182. The valve body 166 has a sleeve cavity 184 extending from the distal end 182 of the valve body 166 to a passage 186 at the proximal end 180 of the sleeve cavity 184. A proximal end of the passage 186 is in fluid communication with the hydraulic fluid reservoir 176. A valve 188 is coupled to the valve body 166 in the passage 186 with a proximal side of the valve 188 in fluid communication with the hydraulic fluid reservoir 176 and a distal side of the valve 188 in fluid communication with a transfer tube 196, which extends through the passage 186, through the proximal end 198 of a plunger sleeve 190, to a plunger lumen 192. A transfer tube seal 199 may be disposed between the transfer tube 196 and the passage 186 that slidably engages the transfer tube 196 to allow the transfer tube 196 to be move axially within the passage 186 while providing a fluid-tight seal.

The plunger sleeve 190 is slidably disposed in the sleeve cavity 184 of the valve body 166 such that the plunger sleeve 190 is movable axially (longitudinally) relative to the valve body 166. The plunger sleeve 190 has a plunger lumen 192 which receives the plunger rod 120 of the syringe 102. The plunger sleeve 190 has a plunger flow passage 194 at the proximal end of the plunger sleeve 190 fluidly connecting the plunger lumen 192 to the transfer tube 196.

The plunger flow passage 194, transfer tube 196, and passage 186 form a hydraulic fluid flow path connecting the hydraulic fluid reservoir 176 to the plunger lumen 192, with the valve 188 in the hydraulic fluid flow path between the hydraulic fluid reservoir 176 and the plunger lumen 192.

The valve 188 is coupled to the valve body 166 such that, when the valve body 166 is in a distal, pre-activation position, e.g., as shown in FIG. 3, the valve 188 is closed thereby preventing hydraulic fluid 174 from flowing between the hydraulic fluid reservoir 176 and the plunger lumen 192. Movement of the valve body 166 axially in a proximal direction to an activation position opens the valve 166 allowing hydraulic fluid 174 to flow between the hydraulic fluid reservoir 176 and the plunger lumen 192 via the hydraulic fluid passage, thereby pressurizing the plunger lumen 192 and pushing the plunger 116 distally.

In exemplary embodiments, the valve 188 may a variable flow control valve 188, which allows a user to vary the flow rate of hydraulic fluid 174 into the plunger lumen 192 such that the user can vary the speed of the movement of the plunger 116 and thus the rate of dispensing the injection fluid 113 out of the syringe 102. The valve 188 is configured to be adjusted to vary the flow rate by adjusting the position of the valve body 166 which adjusts the opening of the valve 188. As described in more detail elsewhere herein, the position of the valve body 166 is adjustable by the user by adjusting an actuator lever 200. As a non-limiting example, the valve 188 may be a needle valve or a pressure-compensated flow control valve. Accordingly, in exemplary embodiments, the flow rate of hydraulic fluid 174 into the plunger lumen 192 when the actuator lever 200 and valve 188 are adjusted may be linear, exponential, polynomial, or other desired profile.

The valve 188 in the illustrated embodiment is a needle valve 188. The needle 202 of the needle valve 188 is attached to the proximal end 180 of the valve body 166. The needle 202 has a tapered shape, tapering from its base distally to its tip. The needle 202 is received in a valve seat 204 (also referred to as a valve orifice 204) when the valve 188 is closed. The valve seat 204 is coupled to the proximal end of the transfer tube 196 (or may even be the proximal end of the transfer tube 196). The valve 188 is opened by moving the valve body 166 proximally using the actuator lever 200, which moves the needle 202 proximally out of the valve seat 204, thereby creating an annular space around the needle 202 through which the hydraulic fluid 174 may pass and enter the transfer tube 196 and plunger lumen 192. The flow rate through the valve 188 is adjusted by adjusting the axial position of the valve body 166 which adjusts the position of the needle 202 relative to the valve seat 204 thereby adjusting the area of the annular space. The area of the annular space determines the flow rate for a give pressure gradient across the valve 188.

Figure 12:
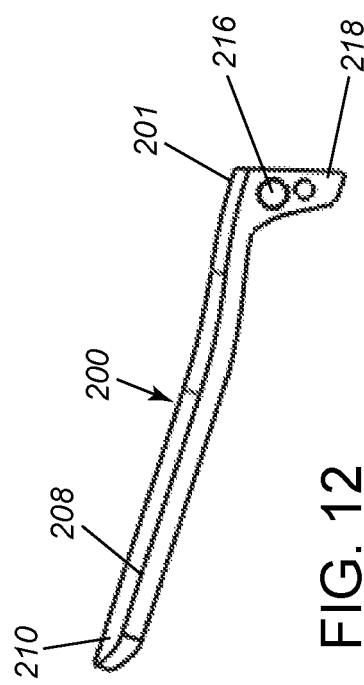
FIG. 12 is an enlarged, side view of a lever of the injection device of FIG. 1, according to one exemplary embodiment.
Figure 13:
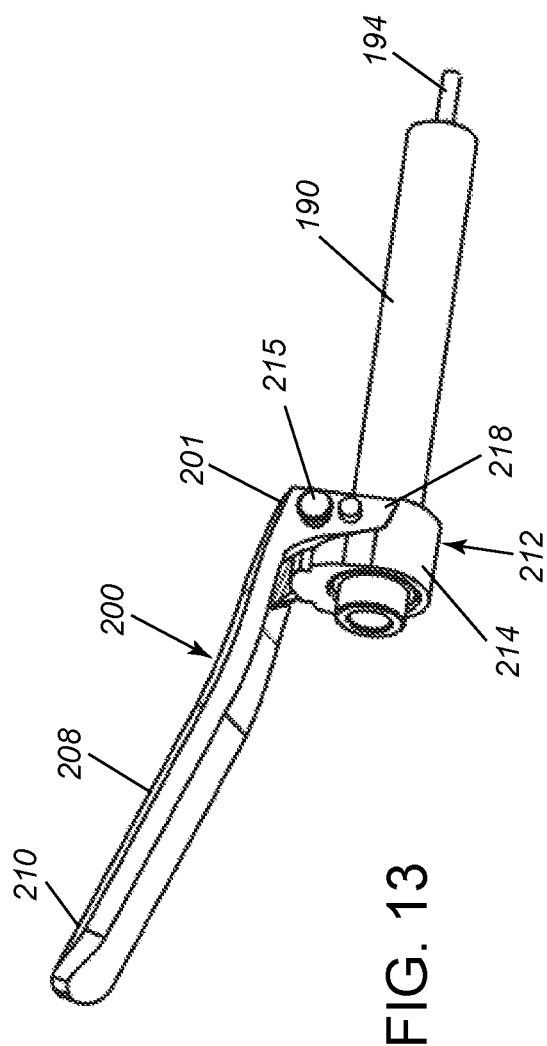
FIG. 13 is an enlarged, side view of a lever, coupler, and plunger sleeve assembly of the injection device of FIG. 1, according to one exemplary embodiment.

The actuator lever 200 is pivotally coupled to the driver housing 134. Enlarged views of the lever 200 is shown in FIGS. 12 and 13. A proximal end 201 of the lever 200 is coupled to the driver housing 134 near the distal end 132 of the drive housing 132 at a pivot joint 206 (see FIGS. 7 and 9-11). The lever 200 has a handle 208 which extends distally from the pivot joint 206 to a distal end 210 of the lever 200.

Figure 2:
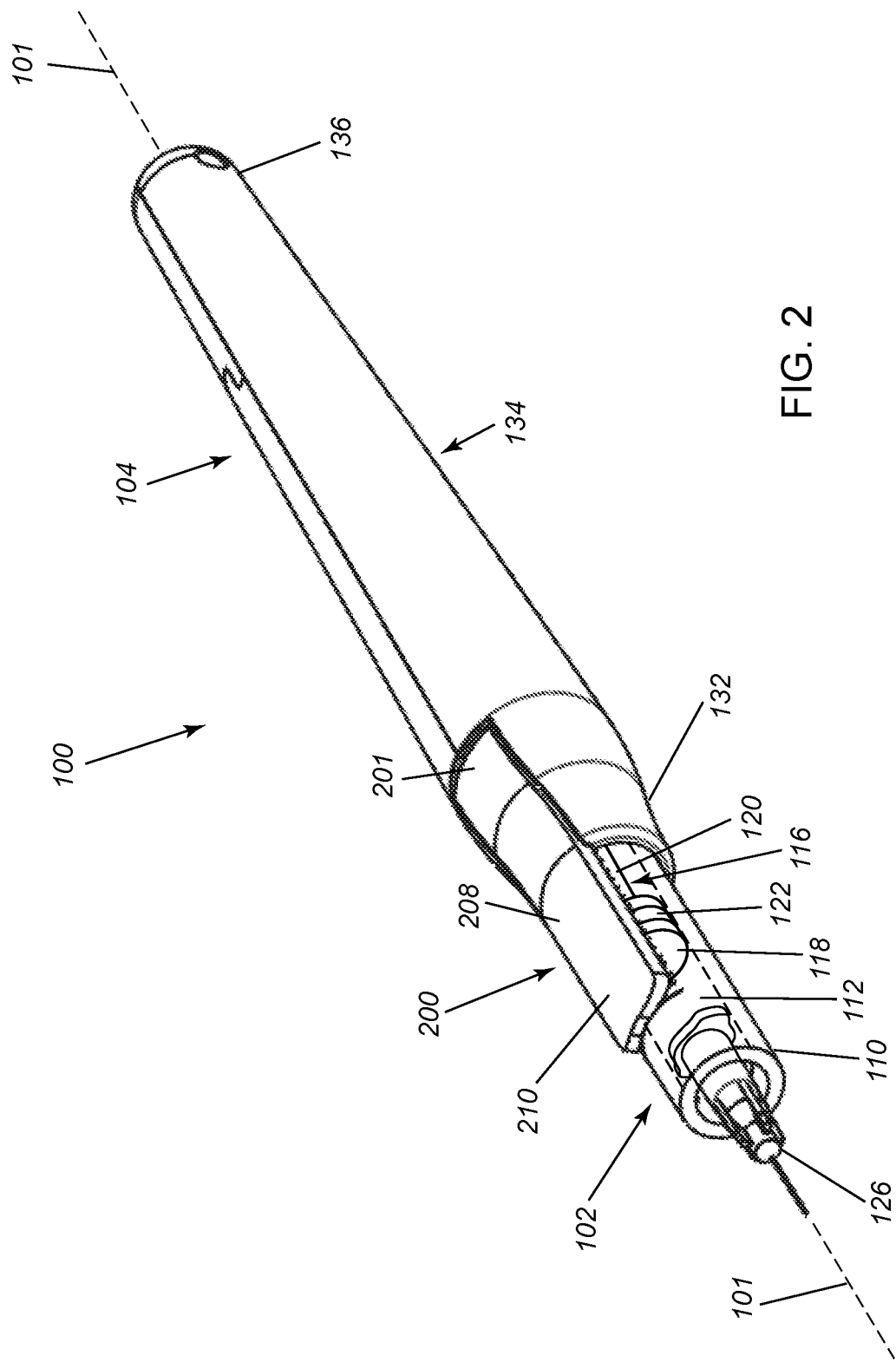
FIG. 2 is a perspective view of the injection device of FIG. 1 in an activation position, according to one exemplary embodiment.
Figure 5:
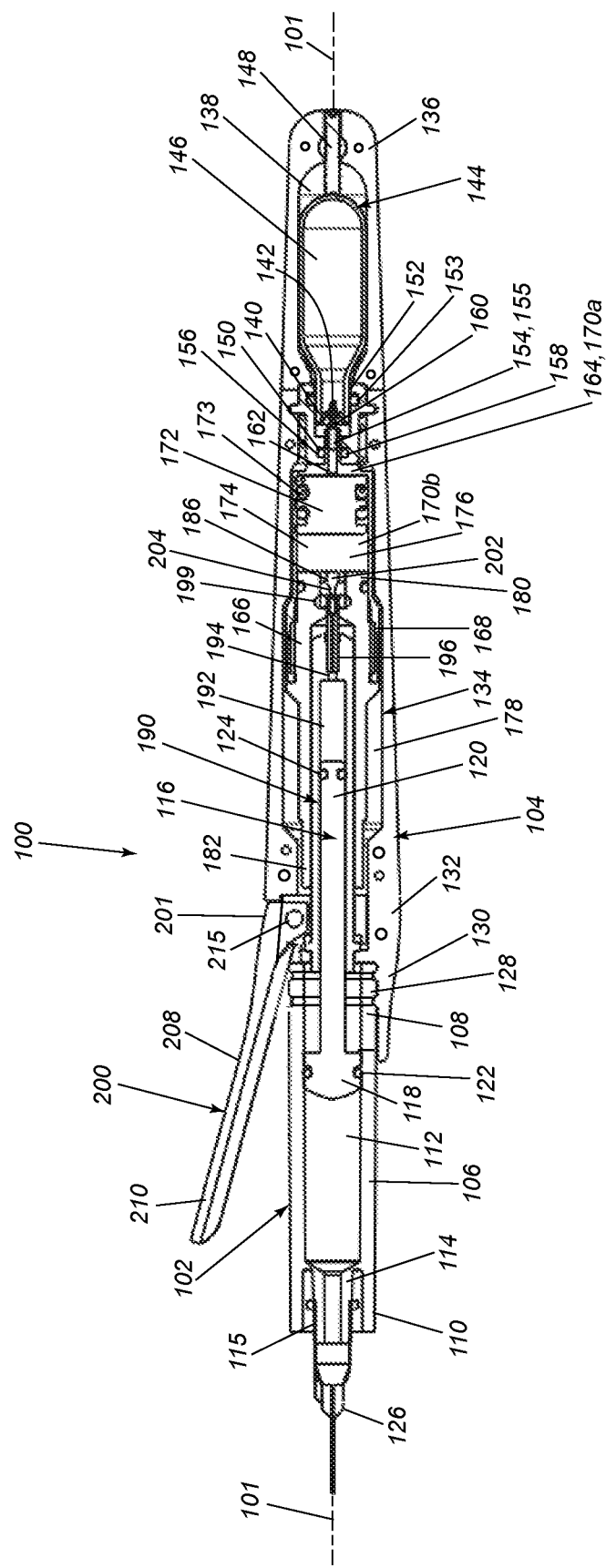
FIG. 5 is a side, cross-sectional view of the injection device of FIG. 1 after it has been activated and the lever has been adjusted to adjust the flow rate, according to one exemplary embodiment.

The lever 200 is coupled to the plunger sleeve 190 via a sleeve coupler 212 (see FIG. 13) and the valve body 166 such that pivotable movement of the lever 200 moves the plunger sleeve 190 and valve body 166 axially. The sleeve coupler 212 has a ring 214 which fits onto the outer surface of the plunger sleeve 190 and a pair of posts 215 (only one of the posts 215 is visible in the view of FIG. 13) extending outward from the ring 214. The posts 215 are rotatingly received in mating holes 216 (see FIG. 12) of the lever 200. The sleeve coupler 212 is coupled to the lever 200 vertically above the pivot joint 206. The lever 200 has a pair of push tabs 218 extending at an angle from the handle portion 208. The push tabs 218 are configured to bear against the distal end 182 of the valve body 166. The push tabs 218 are positioned opposite the pivot joint 206 vertically below the pivot joint 206 such that pivoting the lever 200 about the pivot joint 206 causes the mating holes 216 and push tabs 218 to move in opposite axial directions, thereby moving the plunger sleeve 190 and valve body 166 in opposite axial directions. Hence, when the handle 208 of the lever 200 is pivoted downward from its pre-activation position as shown in FIGS. 1 and 3 (handle 208 pivoted away from the axis 100) toward the activation position, e.g., as shown in FIGS. 2 and 5 (handle 208 pivoted down toward the axis 100), thereby pivoting the lever 200 in a counter-clockwise direction (in the orientation of the injection device 100 as shown in the figures), the lever 200 moves the valve body 166 axially in the proximal direction and the plunger sleeve 190 axially in the distal direction. Conversely, when the lever 200 is moved from the activation position toward the pre-activation position, thereby pivoting the lever 200 in a clockwise direction (in the orientation of the injection device 100 as shown in the figures), the lever 200 allows the valve body 166 to move axially in the distal direction (the push tabs 218 are moved distally away from the distal end 182 of the valve body 166 and the valve body 166 is moved distally by the force of a valve body biasing spring 222, described below) and the lever 200 moves the plunger sleeve 190 axially in the proximal direction.

The syringe driver 104 has a lever biasing spring 220 disposed between the lever 200 and the plunger sleeve 190. The lever biasing spring 220 biases the lever 200 in the upward direction toward the pre-activation position. The syringe driver 104 also has a valve body biasing spring 222 (see FIG. 7) disposed between the bulkhead member 150 and the actuation housing 168. The actuation housing 168 is attached to the valve body 166 such that the valve body biasing spring 168 biases the valve body 166 axially in the distal direction (toward its pre-activation position). The lever biasing spring 220 and valve body biasing spring 222 act in concert, such that, when the lever 200 is released (i.e., a user is not exerting force pushing the lever 200 downward toward the activation position), the lever biasing spring 220 pivots the lever 200 upward toward the pre-activation position and the valve body biasing spring 222 moves the valve body 166 distally. At the same time, the upward pivoting of the lever 200 moves the plunger sleeve 190 axially in the proximal direction and allows the valve body 166 to move axially in the distal direction by the force of the valve body biasing spring 222.

With reference to the FIGS. 1-12, the operation of the injector device 100 will now be described. As shown in FIGS. 1, 3 and 9, the injector device 100 is in a pre-activation position with the plunger 118 in its distal position and the syringe cavity 112 filled with an injection fluid 113 to be dispensed and/or injected (FIG. 1 does not show the plunger 118 in its distal, pre-activation position so that it is visible in the perspective view). A canister 144 of pressurized gas is installed in the pressurized gas chamber 138 with the septum 142 sealing the canister 144. The lever 200 is in its upward, pre-activation position, and the valve body 166 is in its distal, pre-activation position which closes the valve 188 and positions the puncture pin assembly 154 such that the puncture point is distal of the septum 142. The plunger sleeve 190 is in its proximal, pre-activation position, the actuation piston 172 is in its proximal pre-activation position, and the hydraulic fluid reservoir 176 is filled with hydraulic fluid 174.

The injector device 100 is actuated by manually depressing the lever 200 downward toward the activation position. As the lever 200 is pivoted downward from its pre-activation position pivoting the lever 200 in a counter-clockwise direction, the lever 200 moves the plunger sleeve 190 axially in the distal direction. As shown in FIG. 10, the lever 200 is in a middle lever position between the pre-activation position and the activation position. The movement of the lever 200 to this middle lever position moves the plunger sleeve 190 axially distally such that the plunger sleeve 190 advances the plunger 116 of the syringe 102 a small amount which ultimately creates space for the plunger 116 to move back when the lever 200 is released from the activation position and returned to the pre-activation position. This is part of the syringe pressure relief feature which will be further explained as the operation of the injector device is described. During this movement, the lever 200 also moves the valve body 166 axially in the proximal direction, but not yet far enough to open the valve 188.

The lever 200 continues to be pivoted downward to the activation position. As shown in FIGS. 2 and 11, when the lever 200 is depressed to the activation position, the lever 200 moves the valve body 166 to its proximal, activation position which moves the puncture point of the puncture pin assembly 154 into the septum 142 thereby puncturing the septum 142 and releasing the pressurized gas in the canister 144 out through the gas outlet 140. At the same time, the proximal movement of the valve body 166 opens the valve 188. The movement of the lever 200 to the activation position also continues moving the plunger sleeve 190 distally to its activation position. The pressurized gas flowing out of the canister 144 flows through the flow path 155 and pressurizes the proximal region 170a of the piston chamber 164, which exerts pressure on the proximal surface of the actuation piston 172, causing the piston 172 to move distally thereby pressurizing the hydraulic fluid 174 in the hydraulic fluid reservoir 176/distal region 170b of the piston chamber 164. This causes the hydraulic fluid 174 to flow through the now open valve 188, through the hydraulic fluid flow path (i.e., passage 186, transfer tube 196 and plunger flow passage 194) into the plunger lumen 192.

The pressurized hydraulic fluid 174 in plunger lumen 192 pushes the plunger 116 distally, which causes the piston 118 to pressurize the injection fluid 113, thereby forcing the injection fluid 113 out through the outlet port 114 and needle 126. While the injection device 100 is dispensing injection fluid 113, the flow rate of dispensing may be adjusted by moving the lever 200 up or down. Moving the lever 200 upward moves the valve body 166 distally, which adjusts the valve 188 to a more closed position, which reduces the flow rate of the hydraulic fluid 174 into the plunger lumen 192, thereby slowing the distal movement of the plunger 116 and reducing the flow rate at which the injection fluid 113 is dispensed from the syringe 102. While dispensing, the lever 200 may be adjusted up and down to adjust the injection fluid dispensing flow rate in this manner. As illustrated in FIG. 5, the piston 116 has moved distally thereby dispensing injection fluid 113, and the lever 200 is adjusted upward from the activation position to adjust the dispensing flow rate.

In order to stop dispensing injection fluid 113, the lever 200 is released and allowed to move back to the pre-activation position by the force of the lever biasing spring 220 and the valve body biasing spring 222, as shown in FIGS. 6-8. As shown in FIGS. 6-8, the piston 116 has been moved distally to dispense injection fluid 113. The pivoting of the lever 200 back to the pre-activation position after dispensing injection fluid 113 moves the plunger sleeve 190 axially in the proximal direction back to its proximal, pre-activation position and allows the valve body 166 to move axially in the distal direction by the force of the valve body biasing spring 222 back to its pre-activation position. The distal movement of the valve body 166 closes the valve 188. The proximal movement of the plunger sleeve 190 while the valve 188 is closed creates space behind the plunger rod 120, which relieves the pressure of the hydraulic fluid 174 in the plunger lumen 192. In turn, the plunger 120 is able to move proximally in response to residual pressure of the injection fluid 113 in the syringe cavity 112 thereby relieving any residual pressure in the syringe cavity 112. This innovative pressure relieve of residual pressure in the syringe 102 prevents unwanted additional injection fluid 113 from slowly flowing out of the outlet port 114 and needle 126 of the syringe 102. Such pressure relief may be particularly useful for viscous fluids, which may store potentially energy during actitation of the device, and consequently express fluid from the syringe 102 if the energy is not relieved.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for delivering one or more agents into a patient's body, comprising:
    a driver housing, the driver housing having a proximal end and a distal end, the driver housing having a gas chamber proximate the proximal end configured to contain a pressurized gas wherein a gas seal seals a gas outlet, a piston chamber adjacent and distal of the gas chamber and having a fluid flow path connecting to the gas outlet, a valve body chamber adjacent and distal of the piston chamber, a hydraulic fluid reservoir adjacent and distal of the piston chamber containing a hydraulic fluid, and a receiver on the distal end of the driver housing configured to attach to a fluid dispensing device;
    a piston slidably disposed in the piston chamber, the piston having a proximal surface exposed to pressure from the gas when delivered from the gas chamber through the gas outlet and a distal surface exposed to the hydraulic fluid in the hydraulic fluid reservoir;
    a valve body slidably disposed in the valve body chamber, the valve body having a proximal end and a distal end, the valve body having a sleeve cavity extending proximally from the distal end of the valve body to a fluid passage at a proximal end of the sleeve cavity, the fluid passage connecting to a valve;
    a plunger sleeve slidably disposed in the sleeve cavity of the valve body such that the plunger sleeve is movable longitudinally relative to the valve body, the plunger sleeve having a plunger lumen for receiving a plunger of a fluid dispensing device, the plunger lumen in fluid communication with the fluid passage such that the valve is in a flow path between the plunger lumen and the fluid passage;
    the valve coupled to the valve body, the valve configured such that when the valve is open the valve allows the hydraulic fluid to flow between the hydraulic fluid reservoir and the plunger lumen via the fluid passage, and when the valve is closed the valve prevents hydraulic fluid from flowing between the hydraulic fluid reservoir and the plunger lumen via the fluid passage, the valve coupled to the valve body such that axial movement of the valve body opens and closes the valve;
    a lever pivotally coupled to the driver housing, the lever coupled to the plunger sleeve and the valve body such that pivotable movement of the lever moves the valve body to open and close the valve and moves the plunger sleeve longitudinally relative to the driver housing.

2. The device of claim 1, wherein the device is configured such that movement of the lever from a pre-activation position, in which the valve body closes the valve and the plunger sleeve is in a pre-activation proximal position, to an activation position opens the gas seal, opens the valve and moves the plunger sleeve distally such that the plunger sleeve moves distally away from the valve, and movement back towards the pre-activation position from the activation position moves the plunger sleeve proximally thereby relieving residual pressure within the sleeve cavity.

3. The device of claim 1, wherein the piston chamber and the piston are substantially cylindrical.

4. The device of claim 3, wherein the sleeve cavity and the plunger sleeve are substantially cylindrical.

5. The device of claim 1, wherein the gas chamber contains a canister of compressible gas and the gas seal is a septum on an opening of the canister of compressible gas.

6. The device of claim 1, further comprising a puncture pin coupled to the valve body such that longitudinal movement of the valve body in response to movement of the lever cause the puncture pin to puncture the gas seal thereby allowing pressured gas contained in the gas chamber to flow into the piston chamber.

7. The device of claim 1, wherein the valve comprises a needle valve and a needle of the needle valve is coupled to the valve body and an orifice of the needle valve is coupled to the plunger sleeve such that relative longitudinal movement of the valve body and plunger sleeve causes the needle valve to open and close.

8. The device of claim 1, wherein the receiver comprises one of the following: a Luer fitting threads, a flange, a connector, and a syringe connector.

9. The device of claim 1, wherein the hydraulic fluid comprises a fluid selected from the group consisting of silicone, glycerin, saline and water.

10. The device of claim 1, wherein the valve is configured to provide proportional flow control of hydraulic fluid through the valve based on a longitudinal position of the valve body positioned by pivotal movement of the lever.

11. The device of claim 1, wherein the device is configured such that:

in a pre-activation state, the lever extends upward from the driver housing, the valve body closes the valve, and the plunger sleeve is in a proximal position in a pre-activation position;

pivoting the lever downward moves the valve body axially thereby opening the gas seal and opening the valve, and also moves the plunger sleeve axially distally, whereby the pressurized gas pressurizes the piston chamber causing the piston to move thereby pressuring the hydraulic fluid such that the hydraulic fluid flows through the valve into the plunger lumen and advancing a plunger received in the plunger lumen distally; and pivoting the lever back upward moves the valve body axially thereby closing the valve, and also moves the plunger sleeve axially proximally thereby relieving residual hydraulic fluid pressure within the plunger lumen.

12. The device of claim 1, further comprising:

a syringe coupled to the driver housing, the syringe comprising:

a syringe housing having a proximal end, a distal end, a syringe cavity extending from the proximal end to an outlet port on the distal end of the syringe housing; and a plunger disposed in the syringe cavity, the plunger having a plunger rod and a plunger piston on a distal end of the plunger rod;

the proximal end of the syringe attached to the receiver of the driver housing; and a distal end of the plunger rod extending proximally out of the syringe cavity and into the plunger lumen of the plunger sleeve.

13. The device of claim 12, wherein the plunger sleeve is coupled to the lever via a coupler.

14. The device of claim 12, wherein the syringe housing is removably attached to the receiver of the driver housing by one of: mating threads, a Luer fitting, a snap-fit, and mating connectors.

* * * * *